(12) United States Patent
Stummann et al.

(10) Patent No.: US 9,718,685 B2
(45) Date of Patent: Aug. 1, 2017

(54) PROCESS AND REACTOR FOR EXOTHERMAL REACTION

(71) Applicant: Haldor Topsøe A/S, Kgs. Lyngby (DK)

(72) Inventors: Troels Dahlgaard Stummann, Copenhagen (DK); Niels Ulrik Andersen, Gentofte (DK); Madhanakrishnan Janardhanan, Harrow (GB); Jens R. Rostrup-Nielsen, Virum (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 15/030,985

(22) PCT Filed: Oct. 24, 2014

(86) PCT No.: PCT/EP2014/072863
§ 371 (c)(1),
(2) Date: Apr. 21, 2016

(87) PCT Pub. No.: WO2015/062986
PCT Pub. Date: May 7, 2015

(65) Prior Publication Data
US 2016/0257562 A1 Sep. 8, 2016

(30) Foreign Application Priority Data
Oct. 28, 2013 (EP) ..................................... 13190406

(51) Int. Cl.
| | | |
|---|---|---|
| *C07C 1/04* | (2006.01) | |
| *C07C 29/151* | (2006.01) | |
| *C07C 29/152* | (2006.01) | |
| *C01B 3/12* | (2006.01) | |
| *C01B 3/16* | (2006.01) | |
| *B01J 8/04* | (2006.01) | |
| *B01J 8/00* | (2006.01) | |
| *B01J 7/00* | (2006.01) | |
| *C07C 29/154* | (2006.01) | |
| *C07C 29/156* | (2006.01) | |
| *C07C 29/157* | (2006.01) | |

(52) U.S. Cl.
CPC ...... *C01B 3/16* (2013.01); *B01J 7/00* (2013.01); *B01J 8/001* (2013.01); *B01J 8/0453* (2013.01); *B01J 8/0492* (2013.01); *C07C 1/041* (2013.01); *C07C 1/043* (2013.01); *C07C 1/044* (2013.01); *C07C 1/0435* (2013.01); *C07C 29/152* (2013.01); *C07C 29/154* (2013.01); *C07C 29/156* (2013.01); *C07C 29/157* (2013.01); *C07C 29/1512* (2013.01); *B01J 2219/185* (2013.01); *B01J 2219/1943* (2013.01); *C01B 2203/0283* (2013.01); *C01B 2203/061* (2013.01); *C01B 2203/062* (2013.01); *C01B 2203/142* (2013.01); *C07C 2523/06* (2013.01); *C07C 2523/28* (2013.01); *C07C 2523/72* (2013.01); *C07C 2523/745* (2013.01); *C07C 2523/75* (2013.01); *C07C 2523/755* (2013.01)

(58) Field of Classification Search
CPC ... B01J 7/00; B01J 8/001; B01J 8/0453; B01J 8/0492; B01J 2219/185; B01J 2219/1943; C01B 3/16; C01B 2203/0283; C01B 2203/142; C01B 2203/061; C01B 2203/062; C07C 1/041; C07C 1/043; C07C 1/0435; C07C 1/044; C07C 29/1512; C07C 29/152; C07C 29/154; C07C 29/156; C07C 29/157; C07C 2523/06; C07C 2523/28; C07C 2523/72; C07C 2523/745; C07C 2523/75; C07C 2523/755

See application file for complete search history.

(56) References Cited

U.S. PATENT DOCUMENTS

| | | | |
|---|---|---|---|
| 5,306,852 A | 4/1994 | Cosyns et al. | |
| 2012/0165418 A1* | 6/2012 | Park .................. | B01J 23/002 518/713 |
| 2012/0178833 A1* | 7/2012 | Clomburg, Jr. ...... | C07C 1/041 518/711 |
| 2012/0195824 A1* | 8/2012 | Van De Graaf ...... | C01B 3/16 423/655 |

FOREIGN PATENT DOCUMENTS

| | | | |
|---|---|---|---|
| CN | 103265394 A | * | 8/2013 |
| EP | 1 114 669 A1 | | 7/2001 |

OTHER PUBLICATIONS

Dayong et al. Patent No. CN103265394A, Aug. 2013, pp. 1-7; English translation.*

* cited by examiner

*Primary Examiner* — Medhanit Bahta
(74) *Attorney, Agent, or Firm* — Blank Rome LLP

(57) ABSTRACT

The present disclosure relates to a reactor and a method of operation for an exothermal process being catalyzed by a catalytically active material receiving a reactant gas and providing a product gas, in which said exothermal process has a heat development having a potential for thermally degrading said catalytically active material, and which exothermal process operates at a temperature at which the reactants and at least 80% or all of the products are present as gases, said method comprising the steps of a) directing the reactant gas to a first zone of a material catalytically active in the exothermal process producing an first product gas, and b) directing the first product gas to a second zone of a material catalytically active in the exothermal process producing a product gas, with the option of fully or partially by-passing either said first zone or said second zone, while directing a non-condensing gas stream having a temperature at least 50° C. lower than the product gas to said by-passed zone, wherein the choice of by-passing said zone is made based on the time of operation or a process parameter reflecting the catalytic activity of the zone of catalytically active material which is not by-passed with the associated benefit of reducing the extent of thermal deactivation of the catalytically active material, and thus increasing the overall lifetime of the catalytically active material.

19 Claims, 3 Drawing Sheets

PROCESS AND REACTOR FOR EXOTHERMAL REACTION

The present invention relates to a catalytic reactor for exothermal processes, and to a method for operating such a reactor.

When an exothermal reaction such as methanation, water gas shift reaction, or methanol synthesis reaction takes place in an adiabatic reactor, the reaction will with fresh catalyst reach the required conversion within a relative small catalyst volume.

However, due to thermal deactivation of catalytically active material caused by e.g. sintering of metals on the material surface due to high operation temperature, excess catalyst may be required, in order to ensure a long operation time.

Still, as the high reaction temperature is in the initial, upstream sections of the reactor the temperature will remain high in the downstream sections of the reactor; a significant amount of catalyst will deactivate and have lost a part of its activity even before it is required for catalyzing the reaction.

A purpose of the present invention is to reduce the amount of catalyst which is exposed to the high temperature before it is required for catalyzing the reaction.

In the field of refinery processes, deactivation of catalyst caused by side products poisoning the catalyst has according to U.S. Pat. No. 5,306,852 been overcome in a reactor for hydrogenation of liquid olefins at a temperature of 80-120° C., in which a reaction stage is separated into multiple steps (catalytic reactors or catalyst beds), where initially the upstream steps are by-passed, and only the most downstream step is used. As the catalyst deactivates, one less upstream step is by-passed and the two most downstream steps are used. This progressive activation of reaction steps is repeated until all steps are activated, and it has the advantage that only the required catalyst beds are subject to deactivation, as the reaction mixture does not contact the other catalyst beds.

Such an operation is well suited for catalyst deactivation caused by catalyst poisons, such as feed impurities or side reaction products. However, where catalyst deactivation is caused by thermal effects such as sintering, the operational scheme in a single reactor (i.e. that of FIG. 2 of U.S. Pat. No. 5,306,852) will not work, since the heat propagates upwards in the reactor by thermal diffusion and/or thermal circulation of hot gas, and will thus after some time result in an equilibrium temperature close to the temperature in the active beds, and thus sintering of idle reactor beds above the active beds. To avoid this, separate reactors are required (i.e. according to FIG. 1 of U.S. Pat. No. 5,306,852), which will add extra cost, or a separate cold feed gas such as hydrogen may be directed to the idle reactor beds.

A similar configuration is proposed in EP 1 114 669 in which the deactivation by dust is avoided by by-passing individual reactor beds.

An additional problem may be condensation of reactants, products or side products, such as water and hydrocarbons on the catalyst, which temporarily or permanently may limit the activity of the catalyst, and finally, especially for high temperature reactions, the temperature of idle catalyst must be sufficient for activation of the catalyzed reaction, in order to ensure a high activity at the time of changing the bypass configuration.

Finally a reactor with reaction zone by-pass requires a means of flow control suited for the conditions. In U.S. Pat. No. 5,306,852 and EP 1 114 669 valves are positioned upstream the reaction zones, which is well suited when operating a process with a hot or corrosive product.

Now, according to the present invention it is proposed to let the reactant gas by-pass the catalyst beds, while ensuring a flow of non-condensing gas at a temperature sufficient for maintaining rapid activation of the idle catalyst beds, but low enough for avoiding thermal deactivation of the idle beds. In this way the deactivation of the unneeded catalyst volume is avoided, but in addition to the prior art also the thermal deactivation and temporary or permanent damage from condensation of e.g. water is also avoided, and accordingly the catalyst life time will be increased, since the idle catalyst is not exposed to the high temperature before it is needed for catalyzing the reaction, while it is ensured that idle beds are always ready for operation.

For the purpose of the present application a reactor is considered which is configurable for having at least two zones, of which at least one is operated as an active zone, and the remainder of zones may be configured for being operated as active zone(s) or as idle zone(s). An active zone is defined as a zone in which a high flow of reactant gas is directed to the zone and an idle (or by-passed or inactive) zone is defined as a zone, in which no reactant gas or a low flow of reactant gas is directed to the zone.

The distinction between the configurations for an active and an idle or by-passed zone is for the present application defined by the ratio between the flows of reactant gas to the zone in question in the flow configuration having the highest flow of reactant gas and the configuration having the lowest flow of reactant gas is at least a factor 2, preferably at least a factor of 5 and most preferably at least a factor of 10. The term by-passed shall thus be construed to mean fully or partially by-passed, and not only construed as an absolute absence of flow.

For the purpose of the present application, deactivation of a catalytically active material shall be understood as a process by which the catalytic activity of said material is reduced.

For the purpose of the present application, thermal deactivation shall be understood as any deactivation mechanism, which is promoted by a high temperature, irrespectively of whether the mechanism of deactivation is a direct effect of temperature, such as a reduction of the active catalytic surface area by e.g. thermal sintering of catalytically active sites resulting in a lower catalytically active surface, or due to a change of thermodynamically chemical state of the active catalytic surfaces, or an indirect effect of temperature, such as increased poisoning, i.e. chemical or physical blocking of the catalytic surface, due to increased side reactions at higher temperatures.

For the purpose of the present application, an ejector is defined as piece of equipment providing a pump effect by converting a motive stream pressure to kinetic energy of the motive and suction streams, which again is converted into pressure for a discharge stream.

For the purpose of the present application, temperature approach of a gas shall be understood as the difference between the actual temperature of the gas and the equilibrium temperature of that gas composition.

For the purpose of the present application, the dew point for a component of a gas shall be understood as the temperature/pressure combination at which the component condenses from the gas mixture.

For the purpose of the present application, the absolute melting temperature of a material shall be understood as the temperature in degrees K where the metal melts. Where a temperature is defined as a fraction of the absolute melting temperature this shall similarly be understood as the temperature which when measured in degrees K has a value which is a fraction of the absolute melting temperature.

For the purpose of the present application, a dispersed active metal compound shall be understood as a material comprising said metal, either in metal form or in a chemically altered state; typically oxidated as a sulfide or an oxide.

For the purpose of the present application, the sour shift process shall be understood as the water gas shift process in the presence of sulfur.

For the purpose of the present application, a double blocking-gas valve shall be understood as a configuration of 3 valves, which may be configured for blocking a gas flow, or allowing a gas flow. When blocking a gas flow, two main valves are closed, and a third pressure valve allows a pressurized gas to a confined intermediate section between said two valves, assisting their blocking. When allowing a gas flow, the pressurized gas is blocked by the pressure valve, and the two main valves are open.

In a broad form the present disclosure relates to a method of operation for an exothermal process being catalyzed by a catalytically active material comprising a dispersed active metal compound, said process converting a reactant synthesis gas to a product gas, in which the peak temperature of said catalytically active material is at least 40% of the absolute melting temperature of said active metal compound, said method comprising the steps of a) directing the reactant gas to a first zone of a material catalytically active in the exothermal process producing an first product gas, and b) directing the first product gas to a second zone of a material catalytically active in the exothermal process producing a product gas, with the option of fully or partially by-passing either said first zone or said second zone, while directing a non-condensing gas stream having a temperature at least 50° C. lower than the product gas to said by-passed zone, wherein the choice of by-passing said zone is made based on the time of operation or a process parameter reflecting the catalytic activity of the zone of catalytically active material which is not by-passed with the associated benefit of reducing the extent of thermal deactivation of the catalytically active material, and thus increasing the overall lifetime of the catalytically active material, in spite of operating the process under conditions which cause deactivation of said catalytically active material. Additional benefits during such by-passing will be that the fewer side products are produced when the active amount of catalyst operating at high temperature is reduced.

In a further embodiment a condensable compound, such as process water, is present as reactant or product in a concentration resulting in a dew point above 50° C., even more preferably in a dew point above 150° C., with the associated benefit of avoiding a condensation of e.g. water or hydrocarbons on the catalytically active material.

In a further embodiment the method comprises one or more additional steps of directing gas to zones of catalytically active material or by-passing said one or more zones, wherein the decisions of by-passing said one or more additional zones are made based on time of operation or process parameters reflecting the catalytic activity of the one or more of the other zones of material catalytically active in the exothermal process with the associated benefit of additional increased lifetime of the catalytically active material.

In a further embodiment the parameter reflecting the catalytic activity is taken from the group of outlet gas temperature, temperature of catalytically active material, and the concentration of one or more of a reactant and a product, such as CO, $CO_2$, $H_2O$, $CH_3OH$ or $CH_4$ with the associated benefit of improved control of the additional increased lifetime of the catalytically active material.

In a further embodiment the exothermal process is taken from the group comprising methanation, water gas shift reaction and methanol synthesis with the associated benefit of these reactions being commercially attractive reactions.

In a further embodiment the catalytically active material comprises zinc, cobalt, molybdenum, nickel, copper or iron, in reduced, oxide or sulfide form with the associated benefit of zinc being a catalytically highly active material in water gas shift reaction, of cobalt and molybdenum being a catalytically highly active material in sour shift reaction, of nickel being a catalytically highly active material in methanation and water gas shift reaction, at a moderate cost, and copper and iron being highly active materials in the water gas shift reaction at moderate and high temperatures respectively.

In a further embodiment the exothermal process is methanation wherein the inlet temperature of the synthesis gas is in the range 300° C. to 400° C. preferably 330° C. to 360° C. with the associated benefit of providing conditions for high reaction rates.

In a further embodiment the exothermal process is water gas shift reaction wherein the inlet temperature of the synthesis gas is in the range 180° C. to 250° C. preferably 190° C. to 210° C., or in the range 300° C. to 400° C. preferably 330° C. to 360° C. with the associated benefit of providing conditions for high reaction rates over a low/medium temperature shift catalyst comprising e.g. copper, over a high temperature shift catalyst comprising e.g. zinc, iron and/or copper or over a sour shift catalyst comprising e.g. cobalt and/or molybdenum respectively.

In a further embodiment the exothermal process is methanol synthesis wherein the inlet temperature of the synthesis gas is in the range 180° C. to 250° C. preferably 190° C. to 210° C. with the associated benefit of providing conditions for high reaction rates over a methanol synthesis catalyst comprising e.g. copper.

In a further embodiment a specific zone of catalytically active material is by-passed if the temperature approach at the exit of the active zone is less than 50° C., less than 20° C., or less than 10° C. with the associated benefit of only by-passing zones of catalytically active material when the catalyzed reaction has proceeded close to equilibrium.

In a further embodiment an amount of purge gas having a flow rate less than 50%, less than 20% or less than 10% of the flow rate of reactant gas, is directed to the by-passed zones of material catalytically active in the exothermal process with the associated benefit of maintaining a controlled gas flow over the by-passed zones, such that temperature and composition is well defined.

In a further embodiment the purge gas comprises product gas and/or product gas having reacted further, such as at least 20%, at least 50% or at least 80% with the associated benefit that product gas is available and already having a sufficiently high temperature for maintaining the temperature of catalytically active material above the temperature required for activation, without having significant potential for the exothermic reaction. Product gas having reacted further may typically be available from further reaction zones downstream the reactor comprising the optionally by-passed reaction zone(s).

In a further embodiment at least an amount of the purge gas acts as a suction gas in an ejector with either pressurized steam or at least a fraction of the reactant gas being the motive gas with the associated benefit of providing the purge gas at sufficient pressure without the operational cost of a compressor, and without requiring a separate feed gas as purge gas.

A further aspect of the disclosure relates to a reactor for an exothermal gaseous process having a reactor inlet and a reactor outlet, a first zone of catalytically active material, having a first zone inlet, and having a first zone outlet, a second zone of catalytically active material having a second zone inlet and having a second zone outlet, said reactor being configurable for directing the flow from the reactor inlet to the first zone inlet, directing the flow from the first zone outlet to the second zone inlet, and directing the flow from the second zone outlet to the reactor outlet and said reactor alternatively being configurable for fully or partially by-passing said first zone or said second zone, where said fully or partially by-passing of said first zone by-is being obtained by directing the flow from the reactor inlet to the first zone inlet, and directing all, or at least 90%, at least 80% or at least 50% of the flow from the first zone outlet to the to the reactor outlet and where said fully or partially by-passing of said second zone by-is being obtained by directing all, or at least 90%, 80% or 50% of the flow from the reactor inlet to the first zone inlet, directing the flow from the first zone outlet to the to the reactor outlet with the associated benefit of enabling an operation where a zone of catalytically active material is only contacted with gas when it is required for sufficient conversion, and thereby with an increased lifetime of the load of catalyst.

In a further embodiment the reactor comprises 1, 2, 3, 4 or 5 additional zones of catalytically active material, configured for being optionally by-passed, with the associated benefit of additional increased lifetime of the catalytically active material.

In a further embodiment the reactor comprises a means of gas flow control for each zone of catalytically active material to be by-passed, positioned upstream said zone of catalytically active material to be by-passed with the associated benefit of directing an appropriate amount of heated, low-reactive gas to the by-passed zones, keeping said by-passed zones ready for operation.

The present disclosure relates to the protection of catalytically active material against deactivation caused by thermal mechanisms. Deactivation may also occur by means of chemical mechanisms in which a catalyst is poisoned or inhibited by the presence of impurities in the reactant feed or by formation of side products during the reaction. Where the deactivation is irreversible, the deactivating substance is called a poison, and where the deactivation is reversible, the deactivating substance is called an inhibitor. Chemical deactivation may be reduced by avoiding contact with the feed or product stream, in which the deactivating substance is present.

Thermal deactivation is caused by physical effects on the catalyst structure. The physical effects typically involve sintering of a catalytically active metal, present in metal form or in an oxidated state e.g. as oxide or sulfide. The catalytically active metal is highly dispersed on the catalytically active material surface. Sintering of such crystallites is dependent on the temperature, the atmosphere and the interaction with the support. Bulk sintering is typically believed to occur above the Tammann temperature, which typically is estimated as half the absolute melting temperature of the dispersed material. Surface sintering may occur at lower temperatures, i.e. above the Hüttig temperature, which is about one third of the absolute melting temperature of the metal. Sintering temperatures may also be lowered due to adsorbant induced sintering, i.e. sintering mediated by increased mobility due adsorption of species in the feed or product gas, as described a.o. for Cu and ZnO catalysts in Rasmussen et al. Journal of Catalysis 293 (2012) 205-214. For a Cu based catalyst, significant sintering phenomena may be observed at temperatures as low as 320-330° C., e.g. at temperatures around 40-45% of the absolute melting temperature, a.o. due to adsorbant induced sintering by means of CuOH and CuCO. For a Ni based catalyst, significant sintering phenomena requires a higher temperature around 590° C., e.g. at temperatures around 50% of the absolute melting temperature.

Thermal sintering is only avoided if the temperature of the catalytically active material is kept below sintering limits. According to the present disclosure this may be obtained for a limited volume, in which no or a very low extent of reaction occurs, while heating by conduction or radiation is reduced or avoided.

The present disclosure is therefore aimed at operating a process which takes place in the presence of a catalytically active material comprising a dispersed active metal, in which the process temperature is above 40% of the absolute melting temperature of the active metal, and involves process steps for by-passing zones of catalytically active material in a manner which also reduces the heating of the by-passed zones, e.g. by cooling with a gas with low reactivity.

BRIEF DESCRIPTION OF THE ACCOMPANYING DRAWINGS

DETAILED DESCRIPTION OF THE PREFERRED EMBODIMENTS

Figure 1:
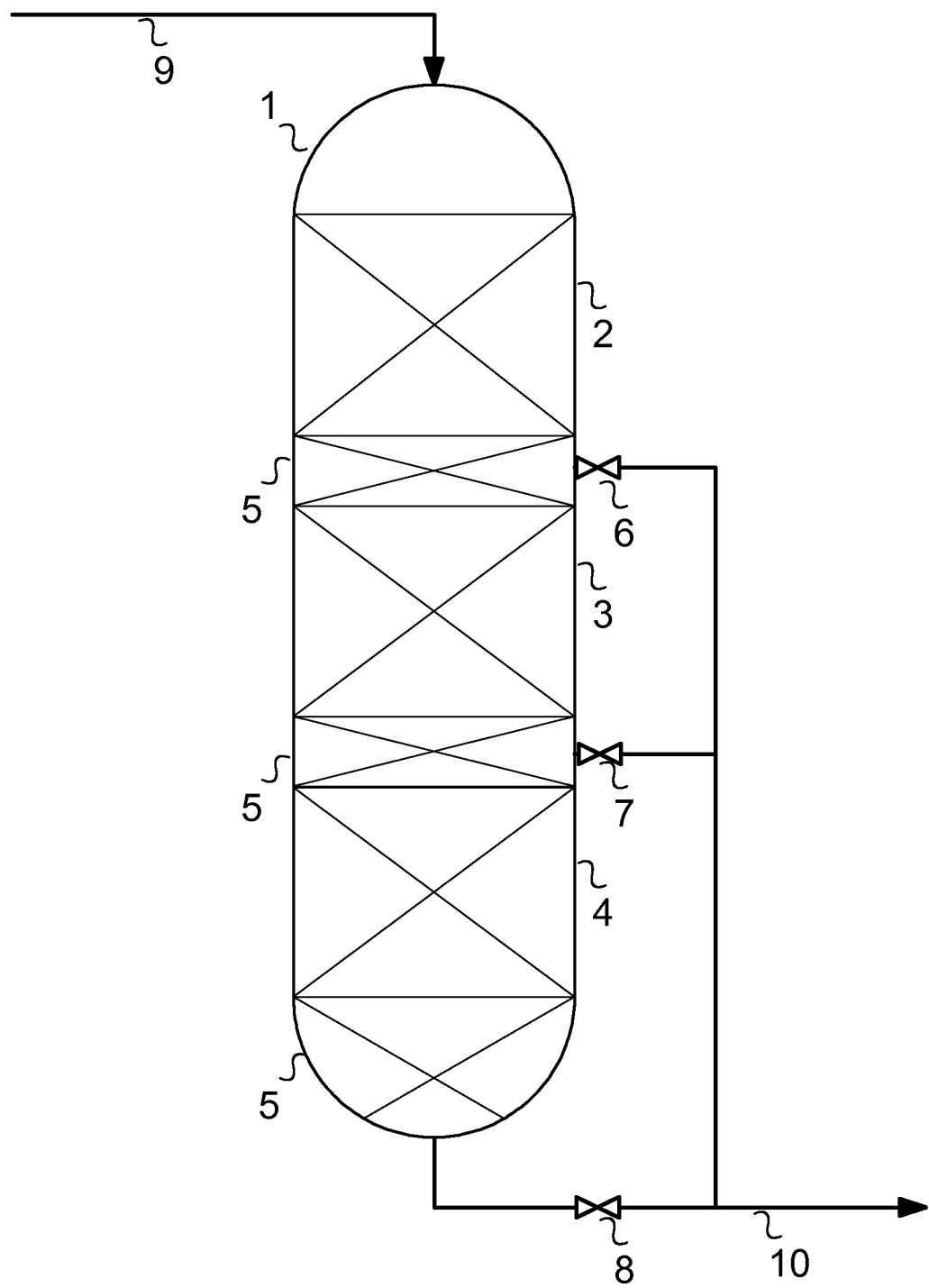
FIG. 1 shows a reactor according to the present disclosure.

In FIG. 1 a reactor is shown, illustrating the present disclosure. The reactor is in the following illustrated by the operation of a process for methanation, but the reactor may beneficially be used for any other exothermal process, including water gas shift, methanol synthesis and Fischer Tropsch synthesis.

In the reactor 1 the catalyst is divided into three sections 2, 3, 4.

After each section a valve and pipe arrangement 6, 7, 8 is found, through which the process gas may be withdrawn. The valve and pipe arrangement or an equivalent means for controlling the withdrawal of process gas can be placed inside or at the outside of the reactor. For a high temperature reaction such as methanation heat stable materials are required for the valves according to this configuration.

During operation, synthesis gas comprising hydrogen and carbon oxides, such as carbon monoxide or carbon dioxide, is directed to the most upstream bed of catalytically active material 2, through line 9. The reactor bed is heated by the exothermal reaction. The valve 6, immediately downstream the active bed 2, is open, and the valves 7,8 downstream the by-passed beds 3,4 are closed. Thereby all reacted gas is withdrawn through 6, and the by-passed beds 3 and 4 are not contacted by heated process gas, and are thus protected against thermal deactivation. When the activity of the active bed has decreased to below a specified threshold, as detected by temperature, composition or other methods, valve 7 is opened and valve 6 is closed, making beds 2 and 3 active and only bed 4 idle. Finally when the combined activity of beds 2 and 3 is below the limit, valve 8 is opened and valve 6 and 7 are closed making all three beds active.

In an alternative to this further disclosure, a purge gas flow may be directed to the by-passed beds (initially 4 and 3) and further to the active reactor outlet 6, to avoid heating of the by-passed beds by a minor leakage of heated gas, and undesired contact between idle catalyst and reactive process gas. This purge gas could be any gas compatible with the catalyst, but typically an inert or low reactivity gas, such as diluted synthesis gas or cooled product gas, would be chosen, to keep the chemical load on the idle catalyst low, while keeping the catalyst temperature at a level where the bed activity is maintained but no significant deactivation takes place.

In an alternative embodiment, a similar maintenance of the bed activity may be obtained if a dilute process gas or an amount of cooled product gas is directed to the by-passed beds via the bottom of the reactor e.g. by directing the purge stream to a position upstream a closed valve 8, and withdrawn together with the product from the active beds.

Such a recycled product stream may be suction stream in an ejector operating with e.g. reactant gas or pressurized steam as motive stream.

In further embodiments an inert layer or a catalyst support grid or a gas extraction arrangement may be installed at the valve or pipe arrangement in order to enable extraction of the process gas and ensure an even gas flow distribution in the section.

Figure 2:
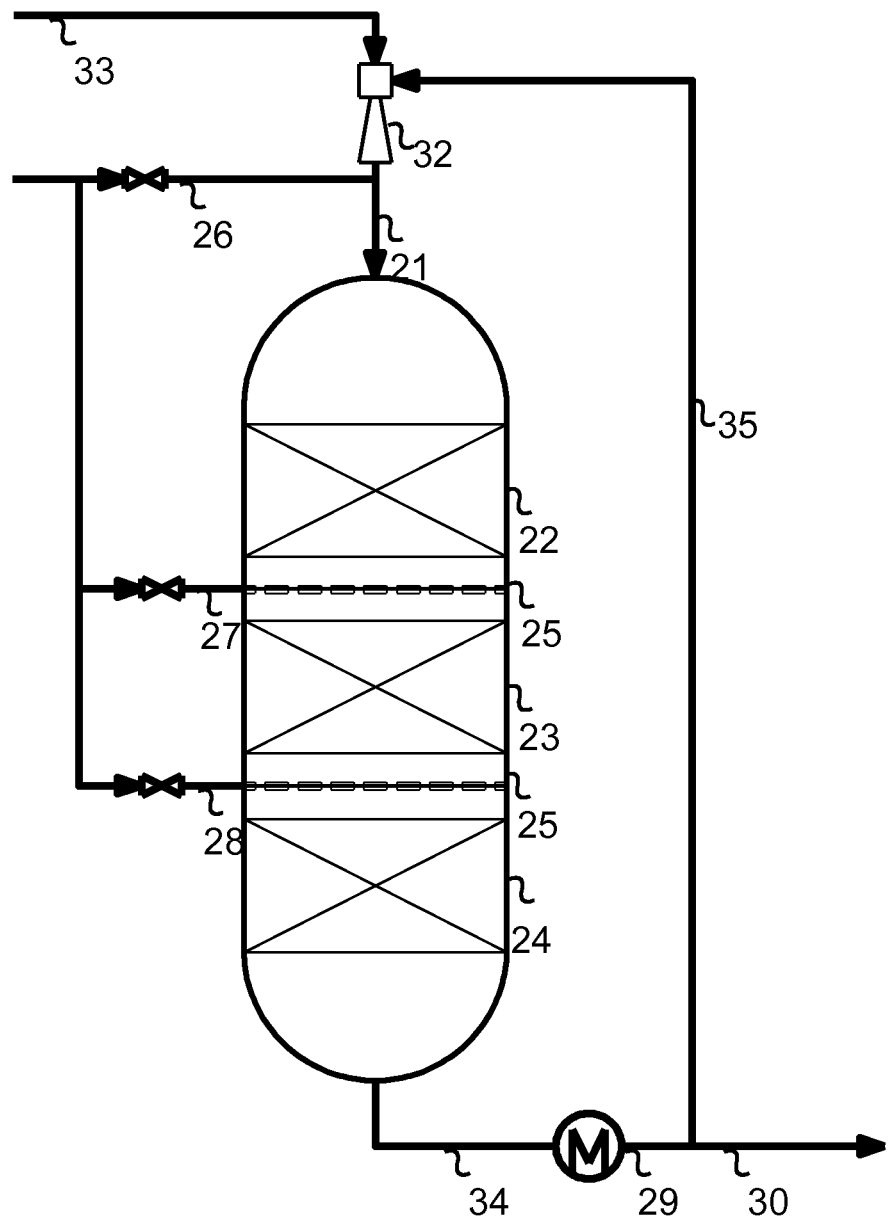
FIG. 2 shows a reactor according to a further embodiment of the present disclosure.

In FIG. 2 a further example of a reactor is shown, illustrating the present disclosure.

In the reactor 21 the catalyst is divided into three sections 22, 23, 24.

Upstream each section a valve and pipe arrangement 6, 7, 8 is found, which controls the flow configuration of the zones of catalytically active material. By placing the valve and pipe arrangement upstream the active reactor beds instead of positioning valves downstream the active reactor beds in a hot position, a requirement for special materials is avoided.

During operation, synthesis gas comprising hydrogen and carbon oxides, such as carbon monoxide or carbon dioxide, is directed to the most downstream bed of catalytically active material 24, through line 28. The reactor bed is heated by the exothermal reaction. To ensure a sufficiently elevated temperature for activating the catalytically active material and a purge for avoiding water condensation, a sub stream of cooled product gas 35 is recycled e.g. driven by an ejector 32 using e.g. reactor reactant gas 33 as motive stream.

The valves 26 and 27 to the idle beds 22 and 23 are closed. Thereby all reacted gas is withdrawn through 34, and the idle beds 22 and 23 are not contacted by heated and/or highly reactive process gas.

When the activity of the active bed has decreased to below a specified threshold, as detected by temperature, composition or other methods, valve 28 is closed and valve 27 is opened, making beds 23 and 24 active and only bed 22 idle. Finally when the combined activity of beds 24 and 24 is below the limit, valve 27 and 28 are closed and valve 26 is opened making all three beds active.

In a further embodiment the product gas may be recycled as suction gas in an ejector using reactant gas as motive stream, the ejector discharge gas has a low reactivity, resulting in an equilibrium temperature of the purge gas being below the critical temperature where significant catalyst deactivation takes place.

Figure 3:
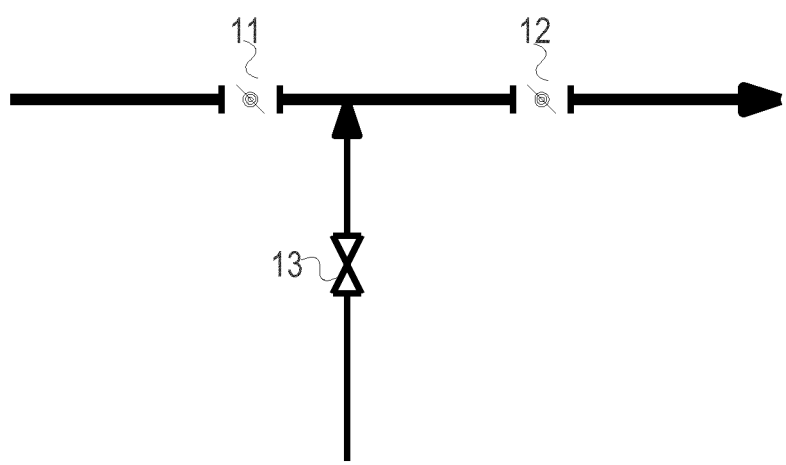
FIG. 3 shows a further embodiment in which the valves are double valves equipped with a blocking gas.

In a further embodiment, the specific valves used may be double blocking gas valves, i.e. double valves equipped with a blocking gas, as indicated in FIG. 3. Valves 11 and 12 are closed, at the same time, and a pressure of a low reactivity gas (e.g. the recycle gas) is provided via valve 13. In this manner valve leakage is minimized by assisting the closing of the valves with the pressure, while using a valve arrangement of moderate cost. This is of higher relevance for the valves downstream the reaction sections, e.g. valves 6, 7 and 8 shown in FIG. 1, where temperatures would by high.

The invention claimed is:

1. A method of operation for an exothermal process being catalyzed by a catalytically active material comprising a dispersed active metal compound, said process converting a reactant synthesis gas to a product gas, in which the peak temperature of said catalytically active material is at least 40% of the absolute melting temperature of said active metal compound, said method comprising the steps of
    a) directing the reactant gas to a first zone of a material catalytically active in the exothermal process producing a first product gas,
    b) directing the first product gas to a second zone of a material catalytically active in the exothermal process producing a second product gas, and
    c) operating said exothermic process to fully or partially by-pass said first zone or said second zone, while directing a non-condensing gas stream having a temperature at least 50° C. lower than the product gas to said by-passed zone, said full or partial by-pass based on the time of operation or a process parameter reflecting the catalytic activity of the zone of catalytically active material which is not by-passed; wherein a condensable compound is present as reactant or product in a concentration resulting in a dew point above 50° C.

2. The method according to claim 1, further comprising one or more additional steps of directing gas to zones of catalytically active material or by-passing said one or more zones, and by-passing said one or more additional zones based on time of operation or process parameters reflecting the catalytic activity of the one or more of the other zones of material catalytically active in the exothermal process.

3. The method according to claim 1, wherein the parameter reflecting the catalytic activity is outlet gas temperature, temperature of catalytically active material, the concentration of one or more of a reactant or a product selected from the group consisting of $CO$, $CO_2$, $H_2O$, $CH_3OH$ and $CH_4$.

4. The method according to claim 1, wherein the exothermal process comprises one of methanation, water gas shift reaction or methanol synthesis.

5. The method according to claim 1, wherein the catalytically active material is one of zinc, cobalt, molybdenum, nickel, copper or iron, in reduced, oxide or sulfide form.

6. The method according to claim 1, wherein the exothermal process is methanation and wherein the inlet temperature of the synthesis gas is in the range of 300° C. to 400° C.

7. The method according to claim 6, wherein the exothermal process is methanation and wherein the inlet temperature of the synthesis gas is in the range of 330° C. to 360° C.

8. The method according to claim 1 wherein the exothermal process is water gas shift reaction and wherein the inlet temperature of the synthesis gas is in the of range 180° C. to 250° C.

9. The method according to claim 8, wherein the exothermal process is water gas shift reaction and wherein the inlet temperature of the synthesis gas is in the range of 190° C. to 210° C.

10. The method according to claim 1, wherein the exothermal process is water gas shift reaction and wherein the inlet temperature of the synthesis gas is in the range of 300° C. to 400° C.

11. The method according to claim 10, wherein the exothermal process is water gas shift reaction and wherein the inlet temperature of the synthesis gas is in the range of 330° C. to 360° C.

12. The method according to claim 1, wherein the exothermal process is methanol synthesis and wherein the inlet temperature of the synthesis gas is in the range of 180° C.

13. The method according to claim 1, wherein the exothermal process is methanol synthesis and wherein the inlet temperature of the synthesis gas is in the range of 180° C. to 250° C.

14. The method according to claim 1, wherein a specific zone of catalytically active material is by-passed if the temperature approach at the exit of the active zone is less than 50° C.

15. The method according to claim 14, wherein a specific zone of catalytically active material is by-passed if the temperature approach at the exit of the active zone is less than 20° C.

16. The method according to claim 1, in which an amount of purge gas having a flow rate less than 50% of the flow rate of reactant gas, is directed to the by-passed zones of material catalytically active in the exothermal process.

17. The method according to claim 16 in which the purge gas comprises product gas and/or product gas having reacted further by at least 20%.

18. The method according to claim 17 in which the at least an amount of the purge gas acts as a suction gas in an ejector with one of pressurized steam or at least a fraction of the reactant gas.

19. The method according to claim 1 in which a condensable compound, is present as reactant or product in a concentration resulting in a dew point above 150° C.

* * * * *